United States Patent [19]
Theriot

[11] Patent Number: 5,892,117
[45] Date of Patent: Apr. 6, 1999

[54] PREPARATION AND USES OF N-METHYLNITRONE

[75] Inventor: Kevin J. Theriot, Baton Rouge, La.

[73] Assignee: Albemarle Corporation, Richmond, Va.

[21] Appl. No.: 873,606

[22] Filed: Jun. 12, 1997

[51] Int. Cl.[6] .................................................. C07C 213/00
[52] U.S. Cl. ......................... 564/347; 564/355; 564/298; 564/299; 548/240
[58] Field of Search ........................... 548/240; 514/646; 564/298, 299, 355, 347

[56] References Cited

U.S. PATENT DOCUMENTS

| | | |
|---|---|---|
| 4,018,895 | 4/1977 | Molloy . |
| 4,596,874 | 6/1986 | Marahashi et al. ...................... 546/141 |
| 5,104,899 | 4/1992 | Young . |
| 5,225,585 | 7/1993 | Schwartz ................................. 585/275 |
| 5,238,959 | 8/1993 | Robertson ............................... 514/604 |

FOREIGN PATENT DOCUMENTS

94/00416  1/1994  WIPO .

OTHER PUBLICATIONS

Arch Pharm Ber Dtsch Ges, by Zinner, pp. 166–173, 1966.
Fornefeld, E. J Org Chem, vol. 44 No. 5 Cycloaddition Reaction with methylnitrone, 1979.
Beilstein BRN 1730816, N, N dimethylhydroxylamine and preparations. Pp. 1–4. Preparation by Zinner, G Arch Pharm Ber Dstch Pharm Ges 299, pp. 163–173, 1966.

Mitsui et al., "Tungstate Catalysed Oxidation of Secondary Amines with Hydrogen Peroxide. A Novel Transformation of Secondary Amines into Nitrones", J. Chem. Soc., Chem. Commun., 1984, pp. 874–875.

Murahashi et al., "Tungsate–Catalyzed Oxidation of Secondary Amines to Nitrones. α–Substitution of Secondary Amines via Nitrones.", J. Org. Chem., 1990, vol. 55, pp. 1736–1744.

*Primary Examiner*—Gary Geist
*Assistant Examiner*—Jean F Vollano
*Attorney, Agent, or Firm*—Philip M. Pippenger

[57] ABSTRACT

Oxidation of secondary amines with hydrogen peroxide and sodium tungstate is reported to give good yields of nitrones. However, when using dimethylamine in this manner, a considerable amount of N,N-dimethylformamide was produced as a co-product. To more selectively produce N-methylnitrone from dimethylamine, a two-step process is used which comprises (a) mixing together dimethylamine and a peroxidic compound, and subjecting the resultant mixture to reaction conditions effective to form a reaction mixture in which N,N-dimethylhydroxylamine has been formed; and (b) mixing together (i) reaction mixture from (a), (ii) a peroxidic compound, and (iii) a transition metal-containing oxidation catalyst, and subjecting the resultant mixture to reaction conditions effective to form a reaction mixture in which N-methylnitrone has been formed. Highest yields of N-methylnitrone are achieved by conducting step (b) at a pH in the range of 7 to about 12, and at a temperature in the range of about −10° to about 100° C.

33 Claims, No Drawings

PREPARATION AND USES OF N-METHYLNITRONE

TECHNICAL FIELD

This invention relates to an improved process for the preparation of N-methylnitrone and its use in the synthesis of N-methyl-3-phenyl-3-[4-trifluoromethyl)phenoxy]propylamine and acid addition salts thereof, such as the racemic hydrochloride salt known generically as fluoxetine hydrochloride, a widely used antidepressant.

BACKGROUND

It is indicated in the literature (U.S. Pat. No. 4,596,874; *J. Chem. Soc., Chem. Commun.*, 1984, 874; and *J. Org. Chem.*, 1990, 55, 1736) that oxidation of secondary amines with hydrogen peroxide and sodium tungstate gives good yields of nitrones. However, when using dimethylamine in this manner, a considerable amount of N,N-dimethylformamide was produced as a co-product. Thus a need exists for a way of more selectively producing N-methylnitrone from dimethylamine.

THE INVENTION

In accordance with this invention N-methylnitrone is produced by a two-step process which comprises (a) mixing together dimethylamine and a peroxidic compound, and concurrently or subsequently subjecting the resultant mixture to reaction conditions effective to form a reaction mixture in which N,N-dimethylhydroxylamine has been formed; and (b) mixing together (i) reaction mixture from (a), (ii) a peroxidic compound, and (iii) a transition metal-containing oxidation catalyst, and concurrently or subsequently subjecting the resultant mixture to reaction conditions effective to form a reaction mixture in which N-methylnitrone has been formed. In order to achieve highest yields of N-methylnitrone in the process, step (b) should be conducted at a pH in the range of 7 to about 12, and at a temperature in the range of about −10° to about 100° C.

By conduct of this process in the proper manner, yields of N-methylnitrone as high as 45%, based on dimethylamine, have been achieved. In contrast, the highest yield achieved utilizing the process approach suggested in the literature was only 20%.

Other embodiments of this invention will become still further apparent from the ensuing description and appended claims.

Step (a)

The reaction between the dimethylamine and peroxidic compound is typically conducted at one or more temperatures in the range of about 0° to about 30° C. Proportions are typically chosen such that from about 1.0 to about 1.2 moles of peroxidic compound are fed to the reaction mixture per mole of dimethylamine being used. Suitable peroxidic compounds include hydrogen peroxide, alkyl hydroperoxides, aryl hydroperoxides, and the like. Aqueous hydrogen peroxide of at least 10% concentration is a preferred reagent for use in the process. Satisfactory yields of N,N-dimethylhydroxylamine are usually achieved within the range of about 0.25 to about 2.0 hours. The reaction is typically conducted in a suitable inert solvent such as water, methanol, ethanol, 2-propanol, or the like, including mixtures of such solvents.

Step (b)

In this step a mixture is formed from (i) reaction mixture from (a), (ii) a peroxidic compound, and (iii) a transition metal-containing oxidation catalyst, and at the same time the mixture is being formed and/or subsequent to the formation of the mixture, the mixture is subjected to one or more temperatures in the range of about 0° to about 30° C. for a period in the range of about 0.1 to about 2.0 hours such that N-methylnitrone is produced in suitable yield. The peroxidic compound is preferably the same as used in step (a), and it is preferred to form the reaction mixture of (b) using a fresh supply of the peroxidic compound. However, it is possible to use in step (b) a different peroxidic compound from that used in step (a). Another variant is to add an excessive quantity of peroxidic compound to the mixture in (a) to serve as the reagent in step (b) as well as in step (a). The transition metal-containing oxidation catalyst charged to the reaction mixture is preferably sodium tungstate. However, other transition metal oxidation catalysts can be used, such as, for example, selenium dioxide, methyltrioxorhenium, and the like. Catalytically effective amounts of the transition metal-containing catalyst typically fall in the range of about 0.1 to about 5.0 mol % based on moles of dimethylamine.

Steps (a) and (b) are preferably conducted in the same reaction vessel, but can be conducted in separate reaction vessels, if desired. Step (b) is typically conducted in the same solvent as used in step (a), but additional solvent can be added in step (b), if desired.

N-methylnitrone can be analyzed in the reaction mixture by $^1$H NMR (internal standard) using solvent suppression techniques.

Examples 1–5, wherein percentages are by weight unless otherwise specified, illustrate the practice and advantages of the above embodiment of this invention, and are not to be construed as constituting limitations on the invention.

EXAMPLE 1

30% Hydrogen peroxide (1.1 g, 9.7 mmol) was added dropwise to 40% aqueous Me$_2$NH (1.0 g, 8.9 mmol) in H$_2$O (7.0 g) with moderate cooling. This mixture was then transferred to an addition funnel and 30% H$_2$O$_2$ (1.1 g, 9.7 mmol), saturated aqueous Na$_2$CO$_3$ (1.1 g), and Na$_2$WO$_4$.2H$_2$O (0.1 g, 1.5 mmol) were added to the flask. The solution in the addition funnel was then added dropwise to maintain the temperature at 40°–50° C. After the addition, the reaction was allowed to cool to 20° C. and analyzed by $^1$H NMR which showed N-methylnitrone as the major product (along with DMF and formaldoxime).

EXAMPLE 2

30% Hydrogen peroxide (17.0 g, 150 mmol) was added dropwise to 40% aqueous Me$_2$NH (13.5 g, 120 mmol) in H$_2$O (94.5 g) with moderate cooling. This mixture was then transferred to an addition funnel and 30% H$_2$O$_2$ (23.5 g, 209 mmol), saturated aqueous NaHCO$_3$ (40 g), and Na$_2$WO$_4$.2H$_2$O (1.3 g, 3.9 mmol) were added to the flask. The solution in the addition funnel was then added dropwise to maintain the temperature at 40°–50° C. After the addition, the reaction was allowed to cool to 20° C. and analyzed by $^1$H NMR which showed N-methylnitrone (30%) as the major product (along with DMF and formaldoxime).

EXAMPLE 3

40% Aqueous dimethylamine (10.0 g, 88.9 mmol) and saturated NaHCO$_3$ (80.0 g) were cooled to 5°–10° C. 50% Hydrogen peroxide (6.0 g, 88 mmol) was added dropwise so as to maintain the temperature <10° C. Na$_2$WO$_4$.2H$_2$O (1.0 g, 3.0 mmol) in H$_2$O 3.0 g) was added dropwise followed by a second addition of H$_2$O$_2$ (6.0 g, 88 mmol). The solution was then analyzed by $^1$H NMR which showed N-methylnitrone as the major product (along with DMF and formaldoxime).

EXAMPLE 4

40% Aqueous $Me_2NH$ (40.0 g, 356 mmol) and saturated aqueous $NaHCO_3$ (160 g) were cooled to 5°–10° C. 50% Hydrogen peroxide (24.0 g, 353 mmol) was added dropwise to maintain the temperature. A solution of 50% Hydrogen peroxide 24.0 g, 353 mmol) and $Na_2WO_4.2H_2O$ (4.0 g, 12 mmol), and saturated aqueous $NaHCO_3$ (160 g) was added dropwise to maintain the temperature. The solution was stirred for several hours. $^1$H NMR analysis showed mainly nitrone formation along with DMF and formaldoxime.

EXAMPLE 5

A solution of 40% aqueous $Me_2NH$ (40.0 g, 356 mmol) and $NaHCO_3$ (12.3 g, 146 mmol) in water (148 g) was cooled to 0° C. 50% Hydrogen peroxide (24.0 g, 353 mmol) was added dropwise to maintain the temperature. A solution of $NaHCO_3$ (12.3 g, 146 mmol) and $Na_2WO_4.2H_2O$ (4.0 g, 12 mmol) in water (148 g) was added slowly. An additional amount of 50% $H_2O_2$ (32.0 g, 471 mmol) was slowly added. $^1$H NMR analysis showed mainly nitrone formation (38%) along with DMF and formaldoxime.

Further embodiments of this invention include: (i) processes for the preparation of 2-methyl-5-phenylisoxazolidine that can be used in the preparation of N-methyl-3-phenyl-3-hydroxypropylamine, (ii) processes for the preparation of N-methyl-3-phenyl-3-hydroxypropylamine that can be used in the preparation of N-methyl-3-phenyl-3-[4-trifluoromethyl)phenoxy] propylamine and acid addition salts thereof, and (iii) processes for the preparation of N-methyl-3-phenyl-3-[4-trifluoromethyl)phenoxy]propylamine and acid addition salts thereof. These embodiments will now be considered seriatim.

Further Embodiment (i)

In this embodiment N-methylnitrone from b) and styrene are mixed together, and subjected to reaction conditions effective to produce a reaction mixture in which 2-methyl-5-phenylisoxazolidine has been formed. If desired, portions of the N,N-dimethylhydroxyl-amine from (a) and/or portions of the N-methylnitrone from (b), can be separated and used for other purposes, and in such case only a portion of such product(s) would be used in the ensuing reaction.

The reaction of N-methylnitrone with styrene results in the formation of 2-methyl-5-phenylisoxazolidine, and when properly performed, 2-methyl-5-phenylisoxazolidine can be produced in high yields. The reaction can be carried out in bulk (no added ancillary solvent) or it can be conducted in an ancillary solvent or diluent such as water, methanol, ethanol, butanol 2-methylpropanol, dioxane, tetrahydrofuran, or the like. Temperatures in the range of about 20° to about 140° C. and reaction periods in the range of about 0.5 to about 24 hours are typical.

The reaction involves one mole of styrene per mole of N-methylnitrone and thus if either reactant is present in less than a stoichiometric amount, it becomes the limiting reactant. Typically the amount of styrene used in forming the reaction mixture will fall in the range of about 1 to about 5 moles per mole of N-methylnitrone being used. It is desirable to stir or otherwise agitate the reaction mixture during at least a substantial portion of the reaction period.

Recovery of 2-methyl-5-phenylisoxazolidine from the reaction mixture can be effected in various ways. One convenient procedure comprises extracting the reaction mixture with a suitable relatively volatile organic solvent such as chloroform, methylene chloride, toluene, ethyl ether, or the like; drying the organic phase with a suitable solid state, neutral or basic, water absorbent such as potassium carbonate, sodium carbonate, sodium sulfate, or the like; removing the absorbent such as by filtration, centrifugation, decantation, or like procedure; and stripping off the solvent and any excess styrene under suitable temperature and pressure conditions.

Example 6 illustrates the practice of this embodiment.

EXAMPLE 6

A mixture of styrene (37.0 g, 356 mmol) and the N-methylnitrone solution from Example 5 is heated at 85° C. for 4 hours. After cooling, the phases are separated and the aqueous phase is extracted with chloroform (2×50 g). The combined chloroform extracts are combined with the initial organic phase, and the resultant mixture is washed with water (50 g). The organic phase is dried $K_2CO_3$) and stripped of chloroform and excess styrene to give 2-methyl-5-phenylisoxazolidine (16 g).

Further Embodiment (ii)

In this embodiment 2-methyl-5-phenylisoxazolidine from Embodiment (i) is subjected to hydrogenation such that N-methyl-3-phenyl-3-hydroxypropylamine is formed. The hydrogenation can be effected by in situ generation of hydrogen, for example by use of finely divided zinc and aqueous acetic acid. Preferably, however, the hydrogenation is effected catalytically by use of hydrogen and a suitable catalyst such as palladium on carbon.

When generating the hydrogen in situ, a mixture consisting essentially of 2-methyl-5-phenylisoxazolidine, water, acetic acid and finely-divided zinc is maintained at one or more temperatures in the range of about 50° to about 100° C. for a sufficient period of time for N-methyl-3-phenyl-3-hydroxypropylamine to be formed in an appropriate yield (e.g., at least 80%). Usually periods in the range of about 1 to about 12 hours will suffice. The amount of acetic acid and finely-divided zinc should be sufficient to generate at least 15% excess hydrogen over the stoichiometric amount required for the reaction.

The catalytic hydrogenation preferably uses 5% or 10% palladium on carbon as catalyst and hydrogen pressures in the range of about 10 to about 100 psig at temperatures in the range of about 20° to about 80° C. However, other suitable hydrogenation catalysts may be used. The reaction should be conducted under essentially anhydrous conditions and thus at least substantially all of the water present in the reaction mixture from c) should be separated or removed, e.g., by a phase cut between the organic and aqueous phases, preferably followed by drying using a suitable solid state, neutral or basic, water absorbent such as potassium carbonate, sodium carbonate, sodium sulfate, or the like. Effective catalytic quantities of palladium-carbon catalyst are typically in the range of about 0.1 to about 5.0 wt % of the weight of the 2-methyl-5-phenylisoxazolidine be used in the reaction. Reaction periods in the range of 2 to about 24 hours are typical, with the lower temperatures and pressures usually requiring the longer reaction periods, and vice versa. Completion of the reaction is indicated by cessation of hydrogen uptake.

Examples 7–10 serve to illustrate ways by which 2-methyl-5-phenylisoxazolidine can be converted into N-methyl-3-phenyl-3-hydroxypropylamine by means of a suitable hydrogenation step.

EXAMPLE 7

2-Methyl-5-phenylisoxazolidine (2.0 g, 12.3 mmol) and Zn powder (1.2 g, 18.3 mmol) in 10 molar aqueous acetic acid are heated to 65°–70° C. for 4 hours. Additional Zn powder (0.4 g, 6.1 mmol) is added and heating is continued for one more hour. The reaction mixture is neutralized with sodium hydroxide and extracted with chloroform. The extract is dried ($K_2CO_3$) and concentrated to give N-methyl-3-phenyl-3-hydroxy-propyl-amine.

EXAMPLE 8

2-Methyl-5-phenylisoxazolidine (12.6 g, 77.3 mmol) in EtOH (134 g) is mixed with 5% Pd/C (1.2 g) in a glass pressure reactor. The reactor is warmed to 40°–50° C. and the pressure maintained at 40 psig with $H_2$ until the pressure becomes constant (ca. 24 hours). The mixture is filtered through Celite and the solvent is removed to give N-methyl-3-phenyl-3-hydroxypropylamine.

EXAMPLE 9

2-Methyl-5-phenylisoxazolidine (38.1 g, 234 mmol) dissolved in tetramethylene sulfone (38.1 g) is mixed with 5% Pd/C (1.9 g) in a glass pressure reactor. The reactor is warmed to 50° C. and the pressure is maintained at 40 psig with $H_2$ for 24 hours. Ethanol (38.1 g) is added and heating is continued for 48 hours. After cooling, the mixture is filtered and the EtOH is removed to give a solution of N-methyl-3-phenyl-3-hydroxypropylamine in tetramethylene sulfone.

EXAMPLE 10

2-Methyl-5-phenylisoxazolidine (54.3 g, 333 mmol) and Pd/C (2.7 g) in EtOH (55.0 g) are heated to 60°–80° C. in a 300-mL, stirred (700 rpm), Hastalloy autoclave which is kept pressurized to 55 psig with $H_2$ for 5 hours. After cooling, the mixture is filtered and the EtOH removed in vacuo to give N-methyl-3-phenyl-3-hydroxypropylamine.

Further Embodiment (iii)

This embodiment of the present invention comprises conducting steps (a) and (b) above, forming 2-methyl-5-phenylisoxazolidine as in Embodiment (i) above, forming N-methyl-3-phenyl-3-hydroxypropylamine as in Embodiment (ii) above, and then reacting N-methyl-3-phenyl-3-hydroxypropylamine so formed with a 4-halobenzotrifluoride to form N-methyl-3-phenyl-3-[(4-trifluoromethyl)phenoxy]propylamine. The 4-halobenzotrifluoride used in the last step of this sequence is preferably 4-fluorobenzotrifluoride or 4-chlorobenzotrifluoride. However, 4-bromobenzotrifluoride or 4-iodobenzotrifluoride, or combinations (or mixtures) of any two or of all four of these 4-halobenzotrifluorides can be used.

The reaction involves one mole of the 4-halobenzotrifluoride per mole of the N-methyl-3-phenyl-3-hydroxypropylamine. Therefore either reactant can be present in excess and the other becomes the limiting reactant. Typically the proportions of these reactants will be in the range of about 1 to about 2 moles of the 4-halobenzotrifluoride per mole of the N-methyl-3-phenyl-3-hydroxypropylamine. The reaction is best performed in a polar aprotic solvent such as sulfolane, N-methylpyrrolidinone, N,N-dimethylformamide, N,N-diethylformamide, N,N-dimethylacetamide, dimethylsulfoxide, or the like, to which a strong base in a finely-divided solid state, such as NaOH or KOH, has been added in an amount in the range of about 1.1 to about 1.5 moles per mole of N-methyl-3-phenyl-3-hydroxypropylamine used. If desired, a phase transfer catalyst such as tetrabutylammonium bromide, cetyltrimethylammonium chloride, tetrabutylammonium hydrogen sulfate, or the like can also be employed, typically in amounts in the range of about 0.1 to about 5.0 wt % based on N-methyl-3-phenyl-3-hydroxypropylamine.

Typically, the reaction is performed at one or more temperatures in the range of about 80° to about 150° C. Reaction periods are typically within the range of about 1 to about 24 hours. Upon completion of the reaction, it is desirable to add water to the mixture and to extract the solution with a suitable solvent such as ethyl ether or methylene chloride which is then washed with water until essentially all of the polar aprotic solvent is removed. Alternatively, the polar aprotic solvent can be removed by distillation, followed by a similar solvent extraction work up. The product is recovered by removal of the solvent, for example by distillation at reduced pressure. The N-methyl-3-phenyl-3-[4-trifluoromethyl)-phenoxy]propylamine can be converted to acid addition salts thereof by conventional procedures. For example, racemic fluoxetine can be formed by treating racemic N-methyl-3-phenyl-3-[4-trifluoromethyl)phenoxy]propylamine with anhydrous hydrogen chloride followed by low temperature crystallization (e.g., in the range of about 0° to about 30° C.) of the racemic fluoxetine from toluene solution.

Examples 11–13 serve to illustrate ways by which N-methyl-3-phenyl-3-[4-trifluoromethyl)phenoxy]propylamine can be formed by reaction between N-methyl-3-phenyl-3-hydroxypropylamine and 4-chlorobenzotrifluoride.

EXAMPLE 11

N-Methyl-3-phenyl-3-hydroxypropylamine (10.7 g, 64.8 mmol), 4-chlorobenzotriflouride (13.0 g, 72.0 mmol), and NaOH (5.5 g, 138 mmol) are dissolved in N-methylpyrrolidinone (100 g), and the solution is heated to 130° C. for 24 hours. After cooling, water (200 mL) is added and the solution is extracted with ether (2×100 mL). The combined ether extracts are washed with water (6×50 mL), dried ($K_2CO_3$) and the solvent is removed in vacuo to give N-methyl-3-phenyl-3-[4-trifluoromethyl)phenoxy]propylamine as a brown oil. The oil is dissolved in toluene (150 mL) and anhydrous HCl is bubbled through the solution until saturated. Upon cooling to 0° C., crystallization occurs to give fluoxetine hydrochloride as a gray solid. The fluoxetine hydrochloride can be further purified by recrystallization from ethyl acetate/cyclohexane.

EXAMPLE 12

N-Methyl-3-phenyl-3-hydroxypropylamine (49.8 g, 302 mmol), 4-chlorobenzotriflouride (60.0 g, 332 mmol), powdered 87% KOH (22.0 g, 341 mmol), and tetrabutylammonium hydrogen sulfate (0.5 g, 1.5 mmol) and sulfolane (47 g) are combined and heated to 150° C. under a nitrogen condenser for 24 hours. More 4-chlorobenzotriflouride (11.0 g, 61 mmol) and KOH (3.0 g, 47 mmol) are added and heating is continued for 48 hours. After cooling, water (300 mL) is added, and the aqueous solution is extracted with ether (3×100 mL) and the combined extracts are washed with water (2×100 mL). The ether solution is dried ($K_2CO_3$). The ether is removed in vacuo and the product is distilled (125°–130° C., 0.5 mm Hg) to give N-methyl-3-phenyl-3-[4-trifluoromethyl)phenoxy]propylamine.

EXAMPLE 13

Powdered KOH (87%, 14.4 g, 257 mmol) is added to a mixture of N-methyl- 3-phenyl-3-hydroxypropylamine (30.8 g, 187 mmol) and 4-chlorobenzotrifluoride (40.0 g, 221 mmol) in N-methylpyrrolidinone (100.0 g). The mixture is heated to 130° C. for 17 hours. The temperature is then raised to 150° C. and more KOH (6.5 g, 116 mmol) is added. Heating is continued for an additional 24 hours. More 4-chlorobenzotrifluoride (10.0 g, 55 mmol) is added and heating is continued for 10 hours. After cooling, water (200 mL) is added and the solution is extracted with $CH_2Cl_2$ (3×100 mL). The extract is washed with water (2×100 mL), dried $K_2CO_3$, and the solvent is removed in vacuo. The crude product is distilled (125°–130° C., 0.5 mm Hg) to give N-methyl-3-phenyl-3-[4-trifluoromethyl)phenoxy]propylamine.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, formed in situ, blended or mixed with one or more other substances, components and/or ingredients in accordance with the present disclosure. Thus the fact that a substance, component or ingredient may have lost its original identity through a chemical reaction or transformation during the course of contacting, in situ formation, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:
   a) adding an aqueous solution of a peroxidic compound to an aqueous solution of dimethylamine and sodium bicarbonate, and maintaining the temperature of the resultant mixture in the range of about 0° to about 30° C. to form a reaction mixture in which N,N-dimethylhydroxylamine has been formed; and
   b) mixing together (i) reaction mixture from a), (ii) a peroxidic compound, and (iii) a transition metal-containing oxidation catalyst, and subjecting the resultant mixture to reaction conditions effective to form a reaction mixture in which N-methylnitrone has been formed.

2. A process according to claim 1 wherein b) is conducted at pH in the range of 7 to about 12, and at one or more temperatures in the range of about −10° to about 100° C.

3. A process according to claim 1 wherein said transition metal-containing oxidation catalyst used in forming the mixture of b) is sodium tungstate or one or more hydrates thereof.

4. A process according to claim 1 wherein said peroxidic compound used in forming the mixture in a) is 10% or more aqueous hydrogen peroxide, and wherein said peroxidic compound used in forming the mixture in b) is 10% or more aqueous hydrogen peroxide.

5. A process according to claim 4 wherein in a) the amount of said hydrogen peroxide used in forming said mixture of a) is about 1 equivalent relative to the amount of dimethylamine used in forming said mixture of a).

6. A process according to claim 1 wherein said peroxidic compound used in forming the mixture in a) is 10% or more aqueous hydrogen peroxide; wherein said peroxidic compound used in forming the mixture in b) is 10% or more aqueous hydrogen peroxide; wherein said transition metal-containing oxidation catalyst used in forming the mixture of b) is sodium tungstate or one or more hydrates thereof; and wherein b) is conducted at pH in the range of 7 to about 12, and at one or more temperatures in the range of about −10° to about 100° C.

7. A process according to claim 6 wherein in a) the amount of said hydrogen peroxide used in forming said mixture of a) is about 1 equivalent relative to the amount of dimethylamine used in forming said mixture of a).

8. A process which comprises:
   a) feeding aqueous hydrogen peroxide solution to an aqueous solution formed from ingredients comprising water, dimethylamine and sodium bicarbonate while maintaining the reaction temperature in the range of about 0° to about 30° C. to form a reaction mixture in which N,N-dimethylhydroxylamine has been formed; and
   b) subjecting a mixture formed from ingredients comprising (i) reaction mixture from a), (ii) a peroxidic compound, and (iii) a transition metal-containing oxidation catalyst to reaction conditions effective to form a reaction mixture in which N-methylnitrone has been formed.

9. A process according to claim 8 wherein b) is conducted at pH in the range of 7 to about 12 and at one or more temperatures in the range of about −10° to about 100° C.

10. A process according to claim 8 wherein said transition metal-containing oxidation catalyst used in forming the mixture of b) is sodium tungstate or one or more hydrates thereof.

11. A process according to claim 8 wherein the solution of hydrogen peroxide used in forming the mixture of a) is 10% or more aqueous hydrogen peroxide, and wherein said peroxidic compound used in forming the mixture of b) is 10% or more aqueous hydrogen peroxide.

12. A process according to claim 11 wherein in a) the amount of said hydrogen peroxide used in forming said mixture of a) is about 1 equivalent relative to the amount of dimethylamine used in forming said mixture of a).

13. A process which comprises:
   a) adding an aqueous solution of a peroxidic compound to an aqueous solution of dimethylamine and sodium bicarbonate, while maintaining the reaction temperature in the range of about 0° to about 30° C. to form a reaction mixture in which N,N-dimethylhydroxylamine has been formed;

b) mixing together (i) reaction mixture from a), (ii) a peroxidic compound, and (iii) a transition metal-containing oxidation catalyst, and subjecting the resultant mixture to reaction conditions effective to form a reaction mixture in which N-methylnitrone has been formed; and c) mixing together N-methylnitrone from b) and styrene, and subjecting the resultant mixture to reaction conditions effective to produce a reaction mixture in which 2-methyl-5-phenylisoxazolidine has been formed.

14. A process according to claim 13 wherein b) is conducted at pH in the range of 7 to about 12, and at one or more temperatures in the range of about −10° to about 100° C.; and wherein c) is conducted at one or more temperatures in the range of about −10° to about 100° C.

15. A process according to claim 14 wherein said transition metal-containing oxidation catalyst used in forming the mixture of b) is sodium tungstate or one or more hydrates thereof.

16. A process according to claim 14 wherein said peroxidic compound used in forming the mixture in a) is 10% or more aqueous hydrogen peroxide, and wherein said peroxidic compound used in forming the mixture in b) is 10% or more aqueous hydrogen peroxide.

17. A process which comprises:

a) adding an aqueous solution of a peroxidic compound to an aqueous solution of dimethylamine and sodium bicarbonate, while maintaining the reaction temperature in the range of about 0° to about 30° C. to form a reaction mixture in which N,N-dimethylhydroxylamine has been formed;

b) mixing together (i) reaction mixture from a), (ii) a peroxidic compound, and (iii) a transition metal-containing oxidation catalyst, and subjecting the resultant mixture to reaction conditions effective to form a reaction mixture in which N-methylnitrone has been formed;

c) mixing together N-methylnitrone from b) and styrene, and subjecting the resultant mixture to reaction conditions effective to produce a reaction mixture in which 2-methyl-5-phenylisoxazolidine has been formed; and d) subjecting 2-methyl-5-phenylisoxazolidine from c) to hydrogenation such that N-methyl-3-phenyl-3-hydroxypropylamine is formed.

18. A process according to claim 17 wherein b) is conducted at pH in the range of 7 to about 12, and at one or more temperatures in the range of about −10° to about 100° C.; and wherein the hydrogenation of d) is effected catalytically by use of hydrogen and a catalytically effective amount of a hydrogenation catalyst.

19. A process according to claim 18 wherein said transition metal-containing oxidation catalyst used in forming the mixture of b) is sodium tungstate or one or more hydrates thereof; and wherein c) is conducted at one or more temperatures in the range of about −10° to about 100° C.

20. A process according to claim 18 wherein said peroxidic compound used in forming the mixture in a) is 10% or more aqueous hydrogen peroxide, and wherein said peroxidic compound used in forming the mixture in b) is 10% or more aqueous hydrogen peroxide.

21. A process which comprises:

a) adding an aqueous solution of a peroxidic compound to an aqueous solution of dimethylamine and sodium bicarbonate, while maintaining the reaction temperature in the range of about 0° to about 30° C. to form a reaction mixture in which N,N-dimethylhydroxylamine has been formed;

b) mixing together (i) reaction mixture from a), (ii) a peroxidic compound, and (iii) a transition metal-containing oxidation catalyst, and subjecting the resultant mixture to reaction conditions effective to form a reaction mixture in which N-methylnitrone has been formed;

c) mixing together N-methylnitrone from b) and styrene, and subjecting the resultant mixture to reaction conditions effective to produce a reaction mixture in which 2-methyl-5-phenylisoxazolidine has been formed;

d) subjecting 2-methyl-5-phenylisoxazolidine from c) to hydrogenation such that N-methyl-3-phenyl-3-hydroxypropylamine is formed; and e) mixing together N-methyl-3-phenyl-3-hydroxypropylamine from d) and 4-halobenzotrifluoride, and subjecting the resultant mixture to reaction conditions effective to produce a reaction mixture in which N-methyl-3-phenyl-3-[(4-trifluoromethyl)phenoxy]propylamine is formed.

22. A process according to claim 21 wherein b) is conducted at pH in the range of 7 to about 12, and at one or more temperatures in the range of about −10° to about 100° C; wherein the hydrogenation of d) is effected catalytically by use of hydrogen and a catalytically effective amount of a hydrogenation catalyst; and wherein in e) the 4-halobenzotrifluoride is 4-chlorobenzotrifluoride.

23. A process according to claim 22 wherein said transition metal-containing oxidation catalyst used in forming the mixture of b) is sodium tungstate or one or more hydrates thereof; and wherein c) is conducted at one or more temperatures in the range of about −10° to about 100° C.

24. A process according to claim 22 wherein said peroxidic compound used in forming the mixture in a) is 10% or more aqueous hydrogen peroxide, and wherein said peroxidic compound used in forming the mixture in b) is 10% or more aqueous hydrogen peroxide.

25. A process which comprises:

a) adding an aqueous solution of hydrogen peroxide to an aqueous solution of dimethylamine and sodium bicarbonate, while maintaining the reaction temperature in the range of about 0° to about 30° C. to form N,N-dimethylhydroxylamine;

b) reacting N,N-dimethylhydroxylamine from a) with a peroxidic compound in the presence of an added transition metal-containing oxidation catalyst to form N-methylnitrone;

c) reacting N-methylnitrone from b) and styrene to form 2-methyl-5-phenylisoxazolidine;

d) hydrogenating 2-methyl-5-phenylisoxazolidine from c) to form N-methyl-3-phenyl-3-hydroxypropylamine; and e) reacting N-methyl-3-phenyl-3-hydroxypropylamine from d) and 4-halobenzotrifluoride to form N-methyl-3-phenyl-3-[(4-trifluoromethyl)phenoxy]propylamine.

26. A process which comprises:

a) adding an aqueous solution of hydrogen peroxide to an aqueous solution of dimethylamine and sodium bicarbonate, while maintaining the reaction temperature in the range of about 0° to about 30° C. to form an N,N-dimethylhydroxylamine-containing reaction mixture; and b) reacting reaction mixture from a) and a peroxidic compound, in the presence of an added transition metal-containing oxidation catalyst, to form a reaction mixture in which N-methylnitrone has been formed.

27. A process according to claim 26 wherein the solution of hydrogen peroxide used in a) is 10% or more aqueous hydrogen peroxide, and wherein said peroxide-compound used in b) is 10% or more aqueous hydrogen peroxide.

28. A process according to claim 27 wherein said added transition metal-containing oxidation catalyst is sodium tungstate or one or more hydrates thereof.

29. A process according to claim 26 which further comprises:

c) reacting N-methylnitrone from b) and styrene to form a 2-methyl-5-phenylisoxazolidine-containing reaction mixture.

30. A process according to claim 29 which further comprises:

d) hydrogenating 2-methyl-5-phenylisoxazolidine from c) to form N-methyl-3-phenyl-3-hydroxypropylamine.

31. A process according to claim 30 which further comprises:

e) reacting N-methyl-3-phenyl-3-hydroxypropylamine from d) and 4-halobenzotrifluoride to form N-methyl-3-phenyl-3-[4-trifluoromethyl)phenoxy]propylamine.

32. A process according to claim 31 wherein the solution of hydrogen peroxide used in a) is 10% or more aqueous hydrogen peroxide, and wherein said peroxidic compound used in b) is 10% or more aqueous hydrogen peroxide.

33. A process according to claim 32 wherein said added transition metal-containing oxidation catalyst of b) is sodium tungstate or one or more hydrates thereof.

* * * * *